United States Patent
Colman et al.

(10) Patent No.: US 12,263,072 B2
(45) Date of Patent: Apr. 1, 2025

(54) DISPOSABLE ABSORBENT ARTICLE WITH SURGE LAYER INCLUDING AT LEAST ONE BARRIER

(71) Applicant: Kimberly-Clark Worldwide, Inc., Neenah, WI (US)

(72) Inventors: Charles W. Colman, Roswell, GA (US); Francis P. Abuto, Roswell, GA (US); Jenny L. Day, Roswell, GA (US); Sridhar Ranganathan, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 808 days.

(21) Appl. No.: 16/615,892

(22) PCT Filed: May 31, 2017

(86) PCT No.: PCT/US2017/035111
§ 371 (c)(1),
(2) Date: Nov. 22, 2019

(87) PCT Pub. No.: WO2018/222178
PCT Pub. Date: Dec. 6, 2018

(65) Prior Publication Data
US 2020/0121524 A1    Apr. 23, 2020

(51) Int. Cl.
*A61F 13/537* (2006.01)
*A61F 13/475* (2006.01)
(Continued)

(52) U.S. Cl.
CPC .... *A61F 13/53704* (2013.01); *A61F 13/4758* (2013.01); *A61F 13/494* (2013.01);
(Continued)

(58) Field of Classification Search
CPC .... A61F 13/4758; A61F 13/49; A61F 13/494; A61F 13/496; A61F 13/537;
(Continued)

(56) References Cited

U.S. PATENT DOCUMENTS

| 3,881,490 A | 5/1975 | Whitehead et al. |
| 4,795,455 A | 1/1989 | Luceri et al. |

(Continued)

FOREIGN PATENT DOCUMENTS

| WO | 0117475 A1 | 3/2001 |
| WO | 2007035038 A1 | 3/2007 |
| WO | 16183709 A1 | 11/2016 |

*Primary Examiner* — Michele Kidwell
(74) *Attorney, Agent, or Firm* — KIMBERLY-CLARK WORLDWIDE, INC.

(57) ABSTRACT

A disposable absorbent article includes a bodyside liner, an outer cover, an absorbent body disposed between the bodyside liner and the outer cover, and a surge layer disposed between the bodyside liner and the absorbent body, the surge layer having an X-Y plane, a Z-direction, and a longitudinal direction, and a barrier extending substantially through the surge material in the Z-direction, wherein the barrier is configured to block at least one linear longitudinal fluid flow path. The surge layer can alternatively have a plurality of barriers extending substantially through the surge material in the Z-direction, wherein the plurality of barriers is configured to block a plurality of linear longitudinal fluid flow paths or all linear longitudinal fluid flow paths while allowing non-linear fluid flow paths in the longitudinal direction.

8 Claims, 5 Drawing Sheets

(51) Int. Cl.
  *A61F 13/494* (2006.01)
  *A61F 13/496* (2006.01)
(52) U.S. Cl.
  CPC ...... *A61F 13/496* (2013.01); *A61F 13/53747* (2013.01); *A61F 2013/53765* (2013.01)
(58) Field of Classification Search
  CPC .......... A61F 13/53704; A61F 13/53747; A61F 2013/53765
  See application file for complete search history.

(56) References Cited

U.S. PATENT DOCUMENTS

| | | | |
|---|---|---|---|
| 5,364,382 A | 11/1994 | Latimer et al. | |
| 5,669,895 A * | 9/1997 | Murakami | A61F 13/5376 604/378 |
| 5,986,167 A | 11/1999 | Arteman et al. | |
| 6,613,028 B1 | 9/2003 | Daley et al. | |
| 6,673,982 B1 | 1/2004 | Chen et al. | |
| 7,189,888 B2 | 3/2007 | Wang et al. | |
| 7,951,127 B2 | 5/2011 | Sanabria et al. | |
| 8,197,455 B2 | 6/2012 | Zander et al. | |
| 9,044,356 B2 | 6/2015 | Ng et al. | |
| 9,173,782 B2 | 11/2015 | Takken et al. | |
| 2003/0106605 A1* | 6/2003 | Jameson | B41J 2/04 141/98 |
| 2003/0120231 A1 | 6/2003 | Wang et al. | |
| 2005/0182374 A1 | 8/2005 | Zander et al. | |
| 2005/0202208 A1* | 9/2005 | Kelly | B32B 27/18 428/131 |
| 2005/0256488 A1 | 11/2005 | Sperl | |
| 2006/0122572 A1* | 6/2006 | Suarez | A61F 13/53708 604/385.101 |
| 2007/0129699 A1 | 6/2007 | Ohtsuka et al. | |
| 2012/0316528 A1 | 12/2012 | Kreuzer et al. | |
| 2014/0358106 A1 | 12/2014 | Tan et al. | |
| 2015/0283003 A1 | 10/2015 | Rosati et al. | |
| 2015/0313766 A1 | 11/2015 | Miao et al. | |
| 2018/0133071 A1* | 5/2018 | Miao | A61F 13/53747 |

* cited by examiner

DISPOSABLE ABSORBENT ARTICLE WITH SURGE LAYER INCLUDING AT LEAST ONE BARRIER

BACKGROUND

The present disclosure relates to disposable absorbent articles, such as those used as personal care products, that accommodate a release of liquid body waste into the article.

Disposable absorbent articles find widespread use as personal care products such as diapers, children's toilet training pants and other infant and child care products, adult incontinence garments and other adult care products, sanitary napkins and other feminine care products and the like, as well as surgical bandages and sponges. These articles absorb and contain body waste and are intended to be discarded after a limited period of use; i.e., the articles are not intended to be laundered or otherwise restored for reuse. Conventional disposable absorbent articles comprise an absorbent body disposed between an inner layer adapted for contacting the wearer's skin and an outer layer for inhibiting liquid waste absorbed by the absorbent body from leaking out of the article. The inner layer of the absorbent article is typically liquid permeable to permit body waste to pass therethrough for absorption by the absorbent body.

For example, wearer's toilet training pants serve as a training aid as a child transitions from diapers to underpants. Conventional toilet training pants are three-dimensional articles, similar to underpants in appearance, but constructed with a liquid permeable inner layer and an absorbent body to provide the absorbent function of disposable absorbent articles. Where the training pants quickly and effectively draw urine away from the skin and retain the urine in the absorbent body, the inner layer of the pants remains dry and comfortable against the child's skin. If the rate of liquid deposited in the article is faster than the rate at which the liquid is drawn away from the skin, liquid can pool in the lowest parts of the article, leading to leakage.

Therefore, despite advancements in the construction of disposable absorbent articles, there continues to be a need for relatively easily constructed disposable absorbent articles capable of absorbing liquid insults with pooling or leakage.

SUMMARY

In one aspect, a disposable absorbent article includes a bodyside liner, an outer cover, and an absorbent body disposed between the bodyside liner and the outer cover. The disposable absorbent article also includes a surge layer disposed between the bodyside liner and the absorbent body, the surge layer having an X-Y plane, a Z-direction, and a longitudinal direction, and a barrier extending substantially through the surge material in the Z-direction, wherein the barrier is configured to block at least one linear longitudinal fluid flow path.

In another aspect, a disposable absorbent article includes a bodyside liner, an outer cover, and an absorbent body disposed between the bodyside liner and the outer cover. The disposable absorbent article also includes a surge layer disposed between the bodyside liner and the absorbent body, the surge layer having an X-Y plane, a Z-direction, and a longitudinal direction, and a plurality of barriers extending substantially through the surge material in the Z-direction, wherein the plurality of barriers is configured to block a plurality of linear longitudinal fluid flow paths while allowing non-linear fluid flow paths in the longitudinal direction.

In yet another aspect, a disposable absorbent article includes s bodyside liner, an outer cover, and an absorbent body disposed between the bodyside liner and the outer cover. The disposable absorbent article also includes a surge layer disposed between the bodyside liner and the absorbent body, the surge layer having an X-Y plane, a Z-direction, and a longitudinal direction, and a plurality of barriers extending substantially through the surge material in the Z-direction, wherein the plurality of barriers is configured to block all linear longitudinal fluid flow paths while allowing non-linear fluid flow paths in the longitudinal direction Other aspects and features of this disclosure will be in part apparent and in part pointed out hereinafter.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Figure 1:
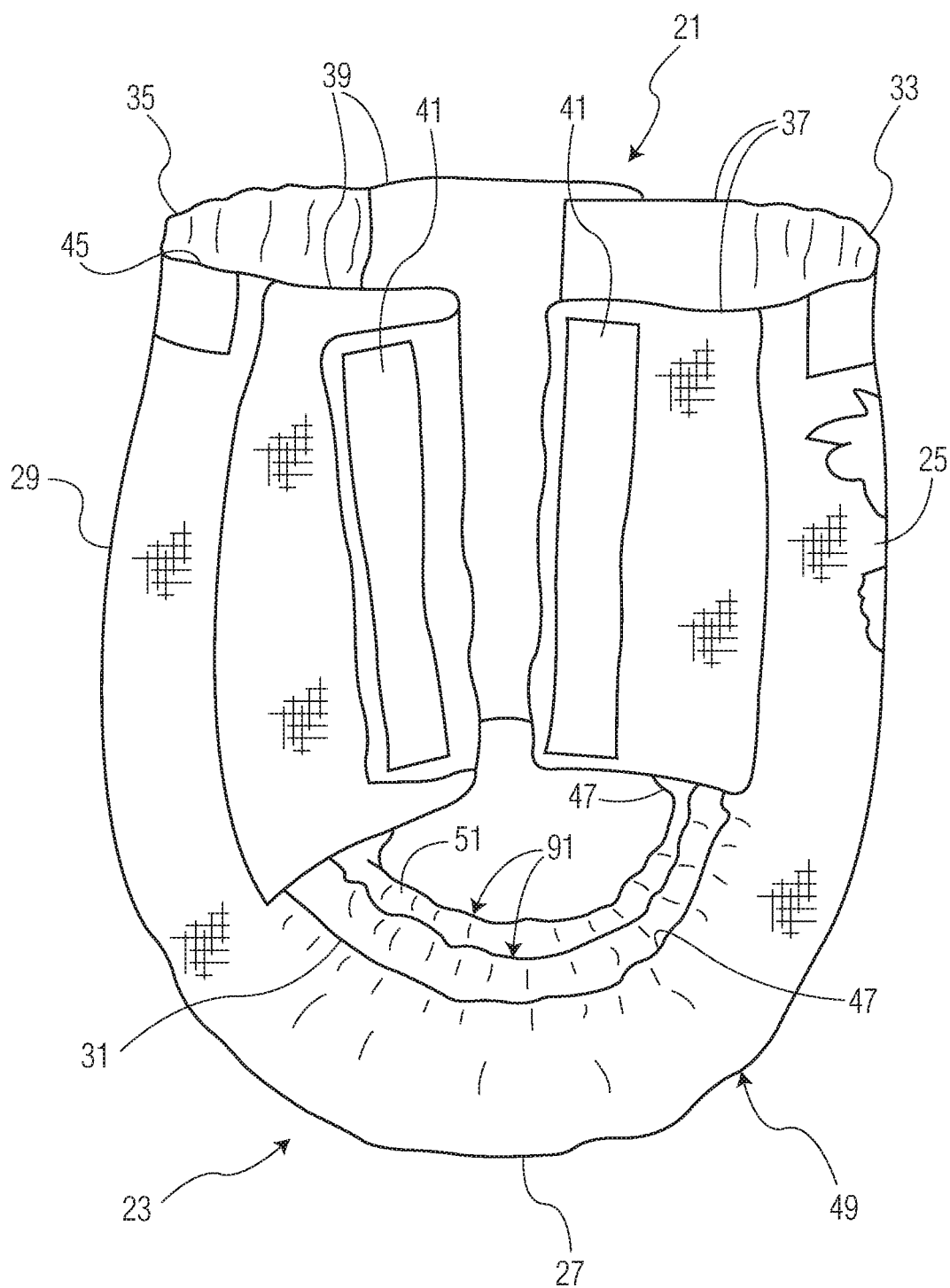
FIG. 1 is a side perspective of wearer's toilet training pants of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

Within the context of this specification, each term or phrase below will include the following meaning or meanings:

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Film" refers to a thermoplastic film made using a film extrusion and/or foaming process, such as a cast film or blown film extrusion process. The term includes apertured films, slit films, and other porous films that constitute liquid transfer films, as well as films that do not transfer liquid.

"Hydrophilic" describes fibers or the surfaces of fibers that are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

"Layer" when used in the singular can have the dual meaning of a single element or a plurality of elements.

"Liquid impermeable" when used in describing a layer or multi-layer laminate means that liquid body waste, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers that can be continuous or discontinuous, are generally smaller than about 0.6 denier, and are generally self bonding when deposited onto a collecting surface. Meltblown fibers used in the present disclosure are preferably substantially continuous in length.

"Non-woven" and "non-woven web" refer to materials and webs of material that are formed without the aid of a textile weaving or knitting process.

"Pliable" refers to materials that are compliant and that will readily conform to the general shape and contours of the wearer's body.

"Spunbond" refers to small diameter fibers that are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

"Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surge Layer" refers to a layer capable of rapidly accepting and temporarily holding liquid body waste to decelerate and diffuse a surge or gush of liquid body waste and to subsequently slowly release the liquid body waste therefrom into another layer or layers.

"Thermoplastic" describes a material that softens when exposed to heat and that substantially returns to a non-softened condition when cooled to room temperature.

"Three dimensional" refers to a garment similar to underwear, shorts or pants in that it has continuous leg and waist openings that are bounded by material of which the garment is made. The garment can have manually tearable seams.

"Tortuosity" refers to the indirectness of a path between two points. For example, a circuitous path from point A to point B has a higher tortuosity than a direct line between point A and point B. A linear path is a straight-line path from point A to point B.

Referring now to the drawings and in particular to FIG. 1, a disposable absorbent article of the present disclosure is shown in the form of wearer's toilet training pants and is indicated in its entirety by the reference numeral 21. As used herein, a disposable absorbent article refers to an article that can be placed against or in proximity to the body (i.e., contiguous to the body) of the wearer to absorb and contain various liquid waste discharged from the body. Such articles are intended to be discarded after a limited period of use instead of being laundered or otherwise restored for reuse. It is understood that the present disclosure is applicable to various other disposable absorbent articles, such as diapers and other infant and child care products, adult incontinence garments and other adult care products, sanitary napkins and other feminine care products and the like, as well as surgical bandages and sponges, without departing from the scope of the present disclosure.

By way of illustration only, various materials and methods for constructing training pants 21 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
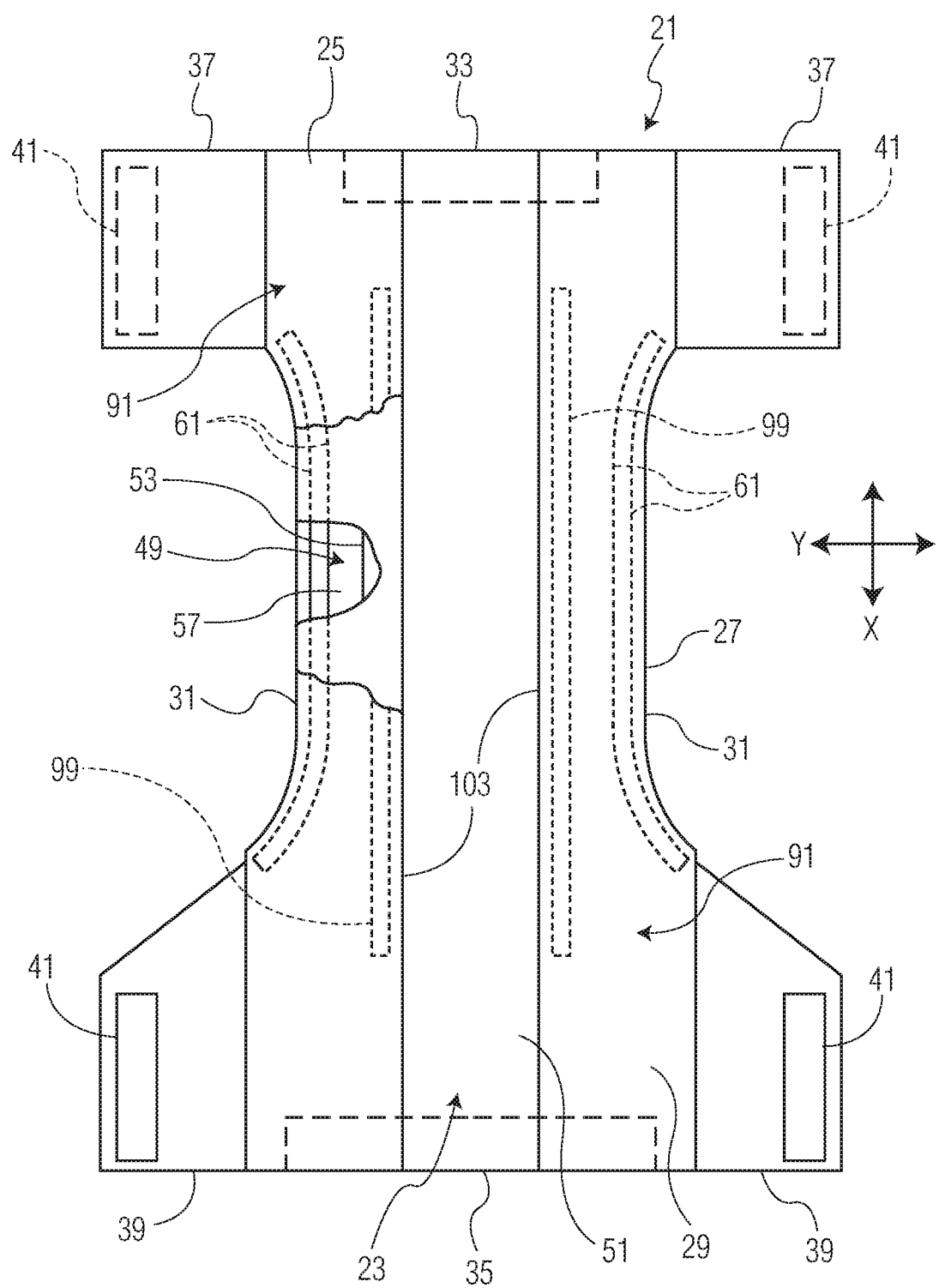
FIG. 2 is a top plan view of the training pants of FIG. 1 with the pants shown unfastened and laid flat and portions of the pants broken away to reveal internal construction thereof.

The training pants 21 of the illustrated embodiment generally comprise a central absorbent assembly 23 extending longitudinally from an anterior region 25 of the training pants through a crotch region 27 to a posterior region 29 of the training pants. As illustrated in FIG. 2, the central absorbent assembly 23 is generally rectangular and has laterally opposite side edges 31 and longitudinally opposite front and rear waist edges, respectively designated 33 and 35. Front and rear side panels 37, 39, respectively, are secured to the central absorbent assembly 23 as will be described later herein and extend laterally outward therefrom respectively at the anterior and posterior regions 25, 29 of the training pants 21.

To form the three-dimensional training pants 21, corresponding front and rear side panels 37, 39 (e.g., the front left side panel and the rear left side panel) are refastenably secured together using fastening assemblies 41. Alternatively, the front and rear side panels 37, 39 can be permanently secured together, such as by ultrasonic bonding, or they can be formed integrally with each other and with the central absorbent assembly 23. Securing the side panels 37, 39 together provides a central waist opening 45 and a pair of laterally spaced leg openings 47 of the training pants 21. The training pants 21 are worn by inserting the wearer's feet through the waist opening 45 and the respective leg openings 47; grasping the training pants near the waist opening; and then pulling the pants up along the wearer's legs until the crotch region 27 of the training pants fits snugly against the crotch of the wearer.

With reference to FIG. 2, the central absorbent assembly 23 of the training pants 21 comprises an outer cover, generally indicated at 49, a bodyside liner 51 and an absorbent body 57 disposed between the outer cover and the liner. The outer cover 49 can be elastic, stretchable or non-stretchable and is desirably a multi-layered laminate structure of which at least one of the layers is liquid impermeable. For example, the outer cover 49 of the illustrated embodiment is of two-layer construction, including an outer layer constructed of a liquid permeable material and an inner layer constructed of a liquid impermeable material joined together by a laminate adhesive. Suitable laminate adhesives, which can be applied continuously or intermittently as beads, a spray, parallel swirls, or the like, can be obtained from Findley Adhesives, Inc., of Wauwatosa, Wisconsin, U.S.A., or from National Starch and Chemical Company, Bridgewater, New Jersey, U.S.A. It is understood that the outer cover 49 can instead be constructed of a single layer of impermeable material without departing from the scope of this disclosure.

The liquid permeable outer layer of the outer cover 49 can be any suitable material and is desirably one that provides a generally cloth-like texture. One example of such a material is a 20 gsm (grams per square meter) spunbond polypropylene non-woven web. The outer layer can also be constructed of the same materials from which the bodyside liner 51 is constructed as described later herein. Also, while it is not a necessity for the outer layer of the outer cover 49 to be liquid permeable, it is desired that it provide a relatively cloth-like texture to the wearer.

The liquid impermeable inner layer of the outer cover 49 can be either vapor permeable (i.e., "breathable") or vapor impermeable. The inner layer is desirably manufactured from a thin plastic film, although other flexible liquid impermeable materials can also be used. The liquid impermeable inner layer (or the liquid impermeable outer cover 49 where the outer cover is of a single-layer construction) inhibits liquid body waste from leaking out of the pants and wetting articles, such as bed sheets and clothing, as well as the wearer and care giver. A suitable liquid impermeable material for such use is a 0.02 millimeter polyethylene film commercially available from Huntsman Packaging of Newport News, Virginia, U.S.A.

Where the outer cover 49 is of single-layer construction, it can be embossed and/or matte finished to provide a more cloth-like appearance. As earlier mentioned, the liquid impermeable layer of the outer cover 49 can permit vapors to escape from the pants 21 while preventing liquids from passing therethrough. A suitable liquid impermeable, vapor permeable material is composed of a microporous polymer film or a non-woven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minnesota, U.S.A.

Leg elastic members 61 are secured between the outer and inner layers of the outer cover 49, such as by being bonded therebetween by laminate adhesive, generally adjacent laterally outer edges of the inner layer of the outer cover. Alternatively, the leg elastic members 61 can be disposed between the outer cover 49 and the bodyside liner 51, or between other layers of the pants 21. A wide variety of elastic materials can be used for the leg elastic members 61. As is well known to those skilled in the art, suitable elastic materials include sheets, strands or ribbons of natural rubber, synthetic rubber, or thermoplastic elastomeric polymers. The elastic materials can be stretched and secured to a substrate, secured to a gathered substrate, or secured to a substrate and then elasticized or shrunk, for example with the application of heat, such that elastic retractive forces are imparted to the substrate. For example, one suitable elastic material is a dry-spun coalesced multifilament spandex elastomeric thread sold under the trade name LYCRA® and available from E.I. du Pont de Nemours and Company, Wilmington, Delaware, U.S.A.

The absorbent body 57 is somewhat rectangular and is desirably constructed to be generally compressible, pliable, non-irritating to the wearer's skin and capable of absorbing and retaining liquid body waste, such as urine. The absorbent body 57 includes an inner layer desirably composed of hydrophilic fibers and an outer layer desirably composed at least in part of a high-absorbency material commonly known as superabsorbent material. More particularly, the inner layer of the absorbent body 57 is desirably composed of cellulosic fluff, such as wood pulp fluff, and the outer layer is desirably composed of superabsorbent hydrogel-forming particles, or a mixture of cellulosic fluff and superabsorbent hydrogel-forming particles. As a result, the inner layer has a lower absorbent capacity per unit weight than the outer layer. The inner layer can alternatively be composed of a mixture of hydrophilic fibers and superabsorbent material, as long as the concentration of superabsorbent material present in the inner layer is substantially lower than the concentration of superabsorbent material present in the outer layer so that the inner layer has a lower absorbent capacity per unit weight than the outer layer. It is also contemplated that the outer layer can be composed solely of superabsorbent material without departing from the scope of this disclosure.

The cellulosic fluff from which the inner layer is composed desirably has a density of about 0.15-0.20 g/cc (grams per cubic centimeter) and constitutes about 20%-80% by weight of the absorbent body. One suitable type of wood pulp fluff is identified with the trade designation CR1654, available from U.S. Alliance, Childersburg, Alabama, U.S.A., and is a bleached, highly absorbent sulfate wood pulp containing primarily soft wood fibers. However, the wood pulp fluff can be exchanged with other hydrophilic fiber materials, such as synthetic, polymeric, or meltblown fibers or with a combination of meltblown fibers and natural fibers.

Suitable superabsorbent materials can be selected from natural, synthetic, and modified natural polymers and materials. The superabsorbent materials can be inorganic materials, such as silica gels, or organic compounds, such as cross-linked polymers. Suitable superabsorbent materials are available from various commercial vendors, such as Dow Chemical Company located in Midland, Michigan, U.S.A., and Stockhausen GmbH & Co. KG, D-47805 Krefeld, Federal Republic of Germany. A surge layer 53 is disposed between the bodyside liner 51 and the absorbent body 57 to help decelerate and diffuse surges or gushes of liquid body waste penetrating the liner 51. The surge layer 53 is similar to that disclosed in U.S. Pat. Nos. 5,490,846 and 5,562,650, the entire disclosures of which are incorporated herein by reference to the extent they do not conflict herewith. The surge layer 53 quickly absorbs surges of liquid body waste that penetrate the liner 51, and then slowly releases the liquid body waste to the absorbent body 57. The surge layer 53 has a width and length substantially the same as the width and length of the absorbent body 57. However, it is understood that the surge layer 53 can be narrower and/or shorter than the absorbent body 57, or wider and/or longer than the absorbent body 57, without departing from the scope of this disclosure.

Desirably, the surge layer 53 can rapidly accept and temporarily hold the liquid body waste prior to slowly releasing the liquid body waste for flow toward the absorbent body 57. The surge layer 53 can include various types of fabrics, such as spunbond fabrics, meltblown fabrics, bonded carded webs, through-air bonded carded webs, knit fabrics, woven fabrics, airformed fabrics and the like, as well as combinations thereof. The fabrics can be composed of various types of fibers, such as polyolefin fibers, polyester fibers, bicomponent fibers, conjugate fibers, and the like, as well as combinations thereof.

For example, one suitable material from which the surge layer 53 can be constructed has a basis weight of about 50 gsm, and includes a through-air-bonded-carded web of a homogeneous blend of 60 percent 3 denier bicomponent fiber including a polyester core/polyethylene sheath, commercially available from KoSa Corporation of Salisbury, North Carolina, U.S.A., and 40 percent 6 denier polyester fiber, also commercially available from KoSa Corporation. Other examples of suitable surge layers 167 are described in U.S. Pat. Nos. 5,486,166; 5,490,846; 5,562,650; and 5,364,382, the entire disclosures of which are hereby incorporated by reference in a manner that is consistent herewith.

The surge layer 53 desirably has a thickness of equal to or greater than about 1.5 mm, and a permeability in the range of about 2000-4000 darcies. The liner 51 is secured to the surge layer 53, such as by being bonded thereto using a suitable adhesive, and to the absorbent body 57, such as by being bonded thereto by additional adhesive. It is understood that the liner 51 can be unsecured to the surge layer 53 and/or to the absorbent body 57 without departing from the scope of this disclosure.

The absorbent body 57 can be wrapped or encompassed by a suitable wrapping (not shown) that maintains the integrity and/or shape of the absorbent body. The absorbent body 57 overlays the outer cover 49, extending laterally between the leg elastic members 61, and is secured to the inner layer, such as by being bonded thereto with adhesive. However, it is understood that the absorbent body 57 can be unsecured to the outer cover 49 and remain within the scope of this disclosure.

The bodyside liner 51 overlays the absorbent body 57 to isolate the wearer's skin from liquid body waste retained by the absorbent body and is secured to at least a portion of the absorbent body, such as by being bonded thereto with adhesive. The liner 51 further extends beyond the absorbent body 57 to overlay a portion of the inner layer of the outer cover 49, particularly in the crotch region 27 of the pants 21, and is secured thereto, such as by being bonded thereto by adhesive, to substantially enclose the absorbent body 57 between the outer cover 49 and the liner 51 about the periphery of the absorbent body 57. Although the bodyside liner 51 is slightly narrower than the outer cover 49, it is understood that the liner 51 and outer cover 49 can be of the same dimensions, or the liner 51 can be sized larger than the outer cover 49, without departing from the scope of this disclosure. It is also contemplated that the liner 51 not extend beyond the absorbent body 57 and not be secured to the outer cover 49 and/or to the absorbent body 57. The bodyside liner 51 is desirably compliant, soft feeling, and non-irritating to the wearer's skin and can be less hydrophilic than the absorbent body 57 to provide a relatively dry surface to the wearer and permit liquid body waste to readily penetrate through its thickness.

The bodyside liner 51 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the bodyside liner 51. For example, the liner 51 can be composed of a meltblown or spunbound web of polyolefin fibers. Alternatively, the liner 51 can be a bonded-carded web composed of natural and/or synthetic fibers. The bodyside liner 51 can also be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from Uniqema, Inc., a division of ICI of New Castle, Delaware, U.S.A, and GLUCOPON® 220UP available from Cognis Corporation of Ambler, Pennsylvania, U.S.A, in an active ratio of 3:1. The surfactant can be applied by any conventional means, such as spraying, printing, brush coating or the like. The surfactant can be applied to the entire liner 51 or it can be selectively applied to particular sections of the liner.

A particularly suitable bodyside liner 51 is constructed of a non-woven bicomponent web having a basis weight of about 27 gsm. The non-woven bicomponent can be a spun-bonded bicomponent web, or a bonded-carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Fibers having other orientations, such as multi-lobe, side-by-side, and end-to-end can be used without departing from the scope of the disclosure. Also, although the outer cover 49 and bodyside liner 51 of the central absorbent assembly 23 can include elastomeric materials, it is contemplated that the central absorbent assembly can instead be generally inelastic, wherein the outer cover 49, the bodyside liner 51, and the absorbent body 57 are composed of materials that are generally non-elastomeric.

The front and rear side panels 37, 39 of the training pants 21 are bonded to the central absorbent assembly 23 at the respective anterior and posterior regions 25, 29 of the pants and extend outward beyond the laterally opposite edges 31 of the assembly. For example, the front side panels 37 of the illustrated embodiment are secured to the inner layer of the outer cover 49, such as by being bonded thereto by adhesive (not shown), by thermal bonding or by ultrasonic bonding. These side panels 37 can also be secured to the outer layer of the outer cover 49, such as by being bonded thereto by adhesive (not shown), by thermal bonding or by ultrasonic bonding. The rear side panels 39 are secured to the outer cover 49 at the posterior region 29 of the training pants 21 in substantially the same manner as the front side panels 37. Alternatively, the side panels 37, 39 can be formed integrally with the central absorbent assembly 23, such as by being formed integrally with the outer cover 49, the bodyside liner 51 or other layers of the pants 21.

For improved fit and appearance, the side panels 37, 39 desirably have an average length measured parallel to the longitudinal axis of the training pants 21 that is about 20 percent or greater, and more desirably about 25 percent or greater, of the overall length of the training pants, also measured parallel to the longitudinal axis. For example, for training pants 21 having an overall length of about 54 centimeters, the side panels 37, 39 desirably have an average length of about 10 centimeters or greater, and more desirably an average length of about 15 centimeters. Each of the side panels 37, 39 can be constructed of one or more individual, distinct pieces of material. For example, each side panel 37, 39 can include first and second side panel portions (not shown) joined at a seam (not shown), with at least one of the portions including an elastomeric material. Alternatively, each individual side panel 37, 39 can be constructed of a single piece of material folded over upon itself along an intermediate fold line (not shown).

The side panels 37, 39 desirably include an elastic material capable of stretching laterally. Suitable elastic materials, as well as one described process for incorporating elastic side panels 37, 39 into training pants 21, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panels 37, 39 can include other woven or non-woven materials, such as those described above as being suitable for the outer cover 49 or bodyside liner 51, or stretchable but inelastic materials.

Containment flaps generally indicated at 91 are secured to the bodyside liner 51 in generally parallel, spaced relation with each other laterally inward of the leg openings to provide a barrier against the flow of urine to the leg openings. The containment flaps 91 extend longitudinally from the anterior region 25 of the training pants 21, through the crotch region 27 to the posterior region 29 of the pants. Each containment flap 91 includes a non-woven layer and a film layer secured to the non-woven layer, such as by being bonded thereto by adhesive. Flap elastics 99 are secured by suitable adhesive between the non-woven layer and the film layer generally at a distal end 103 of the flap 91, with the non-woven layer being folded over the flap elastics 99 and the film layer at the distal end 103. The flap 91 is secured to the bodyside liner 51 by a seam of adhesive to define a proximal end of the flap.

In use, when the wearer of the training pants 21 urinates therein, urine penetrates the liner 51 where the surge layer 53 helps to decelerate and diffuse surges or gushes of liquid body waste penetrating the liner 51 to be absorbed by the absorbent body 57. Unabsorbed urine can be maintained within the surge layer 53. Eventually, urine flows along and through the surge layer 53 to the absorbent body 57. This typical arrangement does not always work in an ideal manner as described below.

All absorbent articles, regardless of the configuration or the number of layers, require several functional tasks to reduce garment leakage. These tasks include fluid intake, fluid distribution, and locking in fluid. Typical personal care absorbent articles address these in part by disposing a surge layer 53 between the liner 51 and the absorbent body 57. The surge material can be a bonded carded web material. The surge layer 53 serves three purposes. 1) Because typical superabsorbent material (SAM) in the absorbent body 57 cannot absorb fluid as fast as the fluid is delivered from the user, the surge layer 53 acts as a temporary holding place or reservoir for the fluid. Therefore, the surge layer 53 should have high permeability and high void volume. 2) When the SAM in the insulted area (generally the anterior region 25) becomes saturated with fluid, additional fluid must transfer via the surge layer 53 to an area where the SAM is not saturated. Therefore, the surge layer 53 must move fluid, or allow fluid to move, in the X-Y plane. 3) After an insult, the surge layer 53 must act as a barrier between the now-wet absorbent layer and the user's skin. Therefore, the surge layer 53 must not permanently hold or "absorb" fluid, which means the surge layer 53 is ideally made of thermoplastic fibers.

If a typical surge material is to 1) have higher permeability in the Z-direction to let fluid pass through; 2) temporarily hold fluid; and 3) be thermoplastic so as to not permanently hold fluid or moisture, then the surge material will also have higher permeability and low capillarity in the X-Y plane. This means that once the SAM in the insult area (generally the anterior region 25) is fully saturated, fluid will run along the surge layer 53 to the lowest point in the absorbent article 21, usually the crotch region 27. After two or three insults the crotch region 27 becomes saturated, and the surge layer 53 does not have the capability to move fluid out of the crotch region 27 against gravity due to its low capillarity. This results in fluid puddling in the crotch region 27 and fluid leakage from the absorbent article 21.

The typical solution to avoid puddling and leakage is to add more absorbent material in the crotch region 27, which also makes the article less comfortable for the user. In addition, because of the many positions the user might be in during insults, extra absorbent material is added in other areas of the article; absorbent material that might not be used depending on the position of the user. Adding extra absorbent material makes the article less comfortable for the user and adds to the cost of the article.

Previous efforts to control fluid in the surge material and increase absorbent core utilization have primarily centered on increasing the capillary tension of the surge material by making a two-layer surge material or by modifying the surfactant treatment of the surge material. Additionally, there has been work on increasing the void volume of the surge material without increasing cost. These have not produced sufficient results.

An alternative and previously-unused means for addressing puddling and leakage is to increase the utilization of absorbent material in the manner described herein. In other words, optimizing fluid flow to use all of the absorbent material already present in the article will eliminate the need to add extra absorbent material. This can be accomplished by controlling fluid flow in the surge layer 53 from the insult point to the lowest point in the absorbent article 21. Reducing the fluid permeability of the surge material in the X-Y plane would slow fluid flow to the low point, but reducing fluid permeability of the surge material in the X-Y plane would change the fluid permeability of the surge material in the Z-direction, leading to less fluid absorption in the absorbent body 57 and a greater amount of fluid resident in the surge layer 53. In addition, reducing fluid permeability of the surge material in the X-Y plane can reduce the fluid flow rate to below that of the flow rate of the insult, causing the fluid to back up over the surge layer 53 and leak. Further, just reducing fluid permeability of the surge material in the X-Y plane would not necessarily increase the contact area of the fluid to unused absorbent.

The surge solution described herein both decreases the flow rate of the fluid from the insult area (generally the anterior region 25) to the low point in the absorbent article 21, and increases the contact of the fluid with the absorbent body 57, thereby enabling a more even distribution of fluid absorption in the absorbent body 57. The surge solution described herein increases the tortuosity of the fluid flow path in the X-Y plane illustrated in FIGS. 3-5 while maintaining both the fluid permeability of the surge material in the X-Y plane and the fluid permeability of the surge material in the Z-direction (perpendicular to the X-Y plane). Forcing the fluid flow into a non-linear path, effectively increasing the path distance from the insult area generally in the anterior region 25 to the crotch region 27, accomplishes the goal of slowing the fluid from reaching the crotch region 27 or other lowest point thus allowing the fluid to be absorbed by the SAM in the absorbent body 53.

The most effective method for increasing the tortuosity of the fluid flow path is to impose barriers 90 to X-Y plane linear fluid flow within the surge layer 53 itself. In one aspect, such barriers 90 can be physical barriers in the form of thin-line embossing placed in various patterns in the surge layer 53. By using heat and pressure, a thin line of highly-densified surge material can be produced such that fluid is prevented from penetrating that line. Such lines can be produced at high speed in a commercial process. As the fluid cannot go through the line, the fluid must go around the line. Any suitable pattern of such lines will slow fluid flow in the X-Y plane. Effective patterns include a series of Vs or chevrons, or a series of lines with strategically-placed line breaks.

In addition to embossments, the barriers can be produced using blocking fillers, chemical (e.g., hydrophobic) treatments, slits, film fragments, polymeric material, adhesive lines, lotions, ointments, or any other suitable means for producing a barrier to fluid flow.

Figure 3:
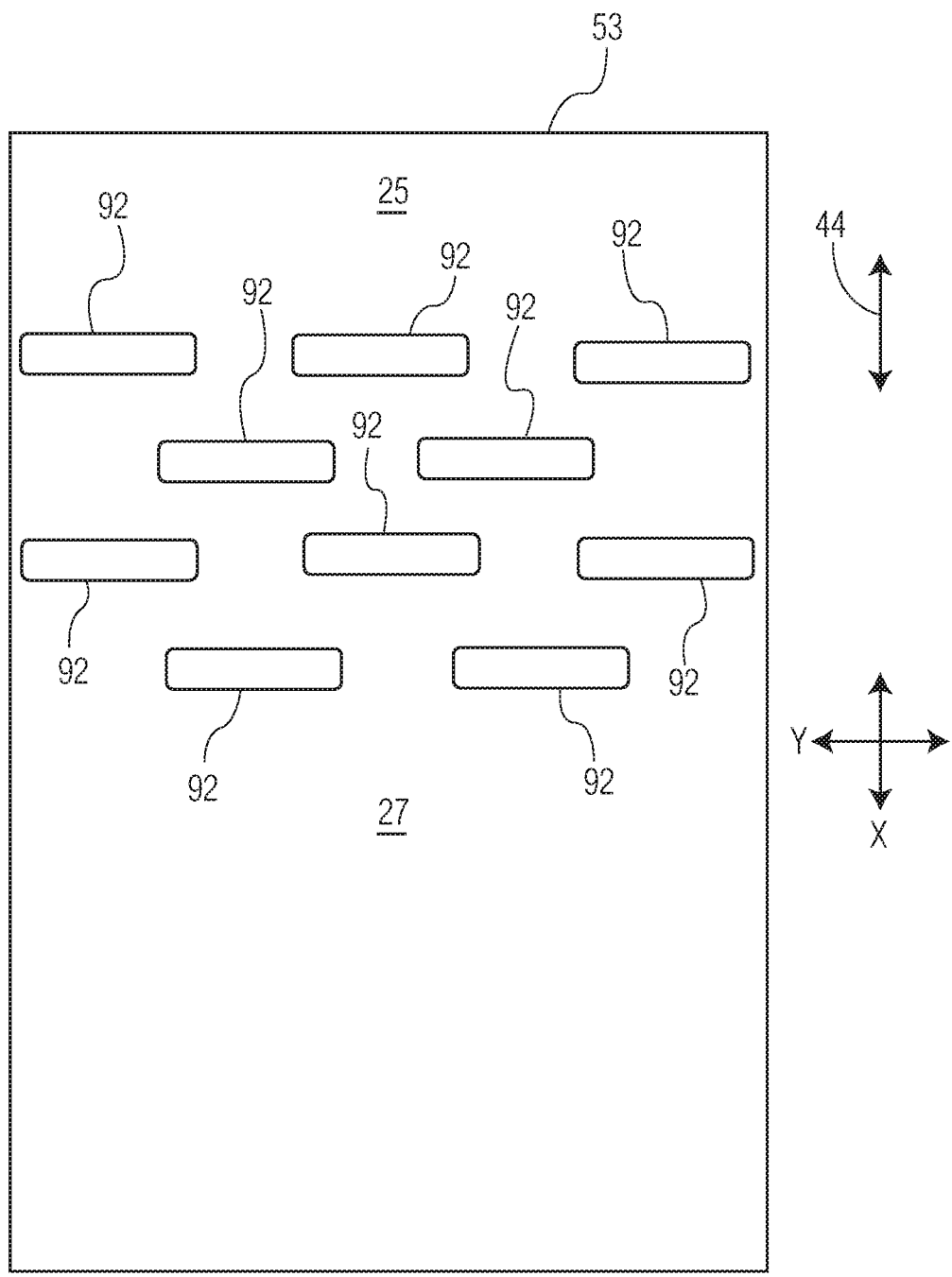
FIG. 3 is a schematic illustration of an embossing pattern in a surge layer from the article shown in FIG. 1.
Figure 4:
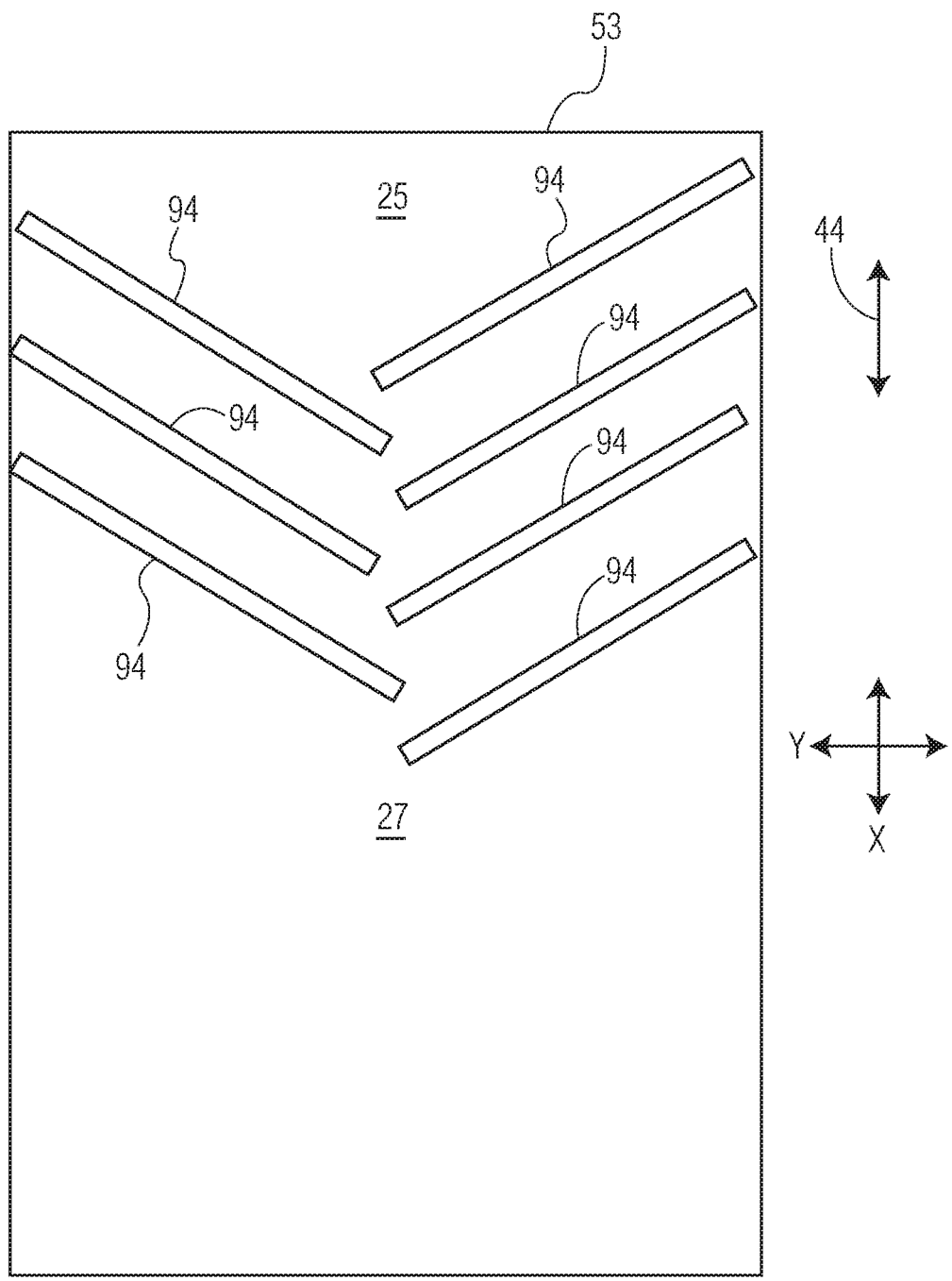
FIG. 4 is a schematic illustration of an alternative embossing pattern in a surge layer from the article shown in FIG. 1.
Figure 5:
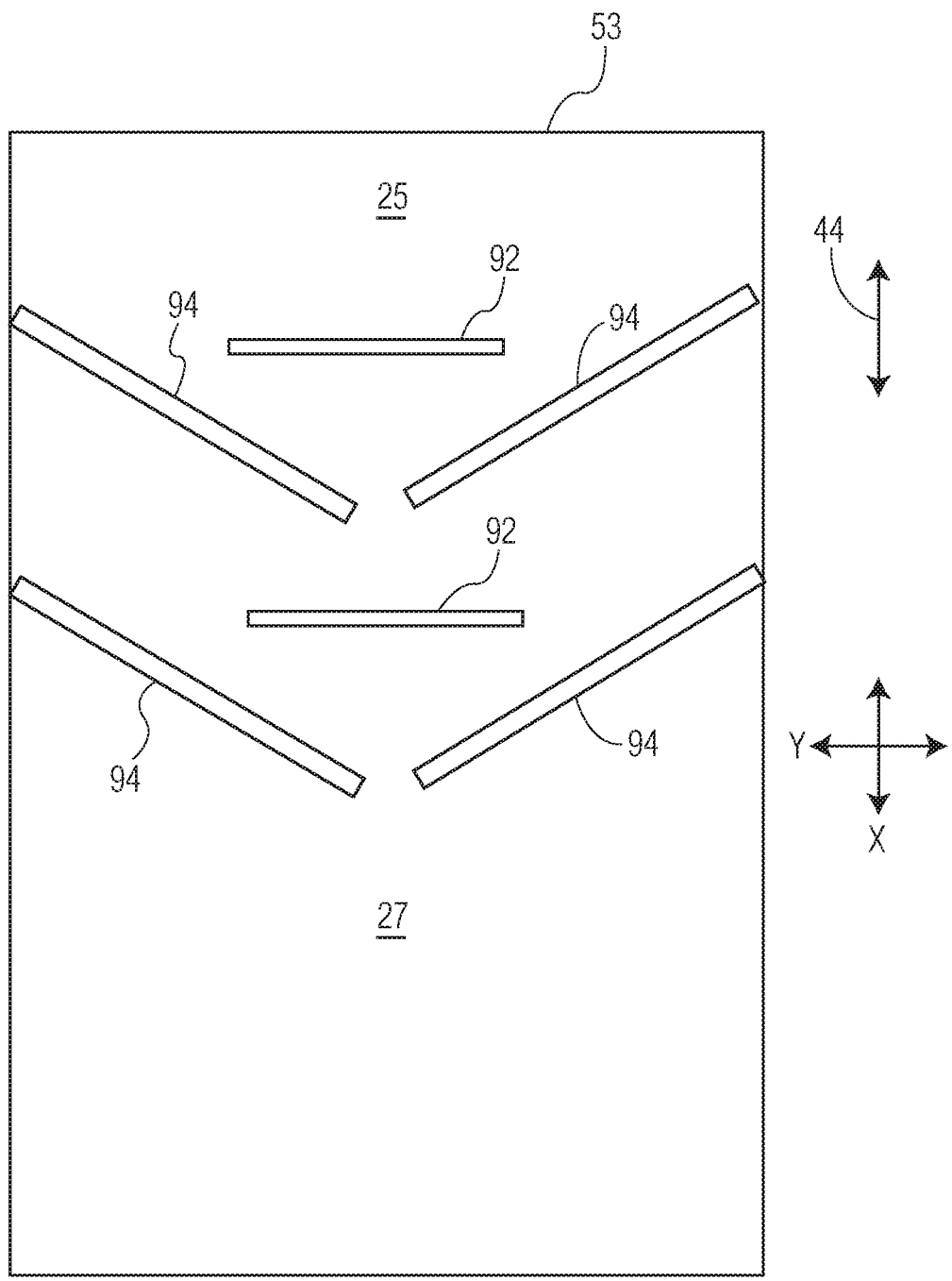
FIG. 5 is a schematic illustration of another alternative embossing pattern in a surge layer from the article shown in FIG. 1.

Three exemplary patterns are illustrated in FIGS. 3-5, which are plan views of a surge layer 53. FIG. 3 shows a pattern of embossed lines 92 through the cross-section thickness or Z-direction of the surge. The embossed lines 92 are staggered to eliminate any linear flow path in the longitudinal direction 44. FIG. 4 shows a pattern of embossed lines in a V pattern 94 also staggered to eliminate any linear flow path in the longitudinal direction 44. FIG. 5 shows a pattern of a combination of embossed lines 92 and embossed lines in a V pattern 94 also staggered to eliminate any linear flow path in the longitudinal direction 44. It should be noted that these are only three examples of suitable patterns. Other suitable patterns can employ arcuate lines, offset geometric shapes, funnel-like patterns, a single line or shape, or any other lines or shapes that reduce or eliminate linear flow paths in the longitudinal direction 44, particularly toward the transverse center of the surge material.

The surge material described herein for use in disposable absorbent articles has increased X-Y tortuosity and fluid flow path, yet still maintains Z-direction permeability. The resultant delay in fluid flow results in more of the fluid being absorbed in the upper portion of the absorbent body 57, rather than running down the surge layer 53 to the lowest point or crotch region 27 of the absorbent body 57, thereby increasing utilization of the absorbent body 57. The increased X-Y tortuosity decreases the amount of fluid in the lower part of an absorbent garment and increases the absorbent core utilization.

In a first particular aspect, an absorbent article includes a bodyside liner; an outer cover; an absorbent body disposed between the bodyside liner and the outer cover; and a surge layer disposed between the bodyside liner and the absorbent body, the surge layer having an X-Y plane, a Z-direction, and a longitudinal direction, and a barrier extending substantially through the surge material in the Z-direction, wherein the barrier is configured to block at least one linear longitudinal fluid flow path.

A second particular aspect includes the first particular aspect, the surge layer further including a plurality of barriers staggered to block a plurality of linear longitudinal fluid flow paths while allowing non-linear fluid flow paths in the longitudinal direction.

A third particular aspect includes the first and/or second aspect, wherein the plurality of barriers includes barriers in the form of parallel lines.

A fourth particular aspect includes one or more of aspects 1-3, wherein the parallel lines are perpendicular to the longitudinal direction.

A fifth particular aspect includes one or more of aspects 1-4, wherein the plurality of barriers includes barriers in the form of lines disposed at a non-orthogonal angle to the longitudinal direction.

A sixth particular aspect includes one or more of aspects 1-5, wherein the plurality of barriers includes a combination of barriers in the form of parallel lines, arcuate lines, and/or geometric shapes.

A seventh particular aspect includes one or more of aspects 1-6, wherein the plurality of barriers includes a plurality of embossments.

An eighth particular aspect includes one or more of aspects 1-7, wherein the article is a diaper, a training pant, an adult incontinent garment, or a menstrual pad.

A ninth particular aspect includes one or more of aspects 1-8, wherein the surge layer comprises thermoplastic fibers.

A tenth particular aspect includes one or more of aspects 1-9, the surge layer further including a plurality of barriers staggered to block all linear longitudinal fluid flow paths while allowing non-linear fluid flow paths in the longitudinal direction.

An eleventh particular aspect includes one or more of aspects 1-10, wherein the barrier is one of an embossment, a blocking filler, a chemical treatment, a slit, a film fragment, a polymeric material, an adhesive, a lotion, an ointments, and combinations thereof.

A twelfth particular aspect includes one or more of aspects 1-11, wherein the barrier is an embossment.

In a thirteenth particular aspect, an absorbent article includes a bodyside liner; an outer cover; an absorbent body disposed between the bodyside liner and the outer cover; and a surge layer disposed between the bodyside liner and the absorbent body, the surge layer having an X-Y plane, a Z-direction, and a longitudinal direction, and a plurality of barriers extending substantially through the surge material in the Z-direction, wherein the plurality of barriers is configured to block a plurality of linear longitudinal fluid flow paths while allowing non-linear fluid flow paths in the longitudinal direction.

A fourteenth particular aspect includes the thirteenth particular aspect, wherein the plurality of barriers includes barriers in the form of parallel lines.

A fifteenth particular aspect includes the thirteenth and/or fourteenth particular aspect, wherein the plurality of barriers includes barriers in the form of a plurality of lines disposed at a non-orthogonal angle to the longitudinal direction.

A sixteenth particular aspect includes one or more of aspects 13-15, wherein the article is a diaper, a training pant, an adult incontinent garment, or a menstrual pad.

A seventeenth particular aspect includes one or more of aspects 13-16, wherein the plurality of barriers includes a plurality of embossments.

An eighteenth particular aspect includes one or more of aspects 13-17, wherein the plurality of barriers include one of an embossment, a blocking filler, a chemical treatment, a slit, a film fragment, a polymeric material, an adhesive, a lotion, an ointments, and combinations thereof.

In a nineteenth particular aspect, an absorbent article includes a bodyside liner; an outer cover; an absorbent body disposed between the bodyside liner and the outer cover; and a surge layer disposed between the bodyside liner and the absorbent body, the surge layer having an X-Y plane, a Z-direction, and a longitudinal direction, and a plurality of barriers extending substantially through the surge material in the Z-direction, wherein the plurality of barriers is configured to block all linear longitudinal fluid flow paths while allowing non-linear fluid flow paths in the longitudinal direction.

A twentieth particular aspect includes the nineteenth particular aspect, wherein the article is a diaper, a training pant, an adult incontinent garment, or a menstrual pad.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there can be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An absorbent article comprising:
   a bodyside liner;
   an outer cover;
   an absorbent body disposed between the bodyside liner and the outer cover; and
   a surge layer disposed between the bodyside liner and the absorbent body, the surge layer having an X-Y plane, a Z-direction, and a longitudinal direction, and a plurality of barriers extending substantially through the surge layer in the Z-direction, wherein the plurality of barriers is configured to block a plurality of linear longitudinal fluid flow paths within the surge layer itself while allowing non-linear fluid flow paths in the longitudinal direction, wherein the plurality of linear longitudinal flow paths that are blocked by the plurality of barriers includes a linear longitudinal flow path through a transverse center of the surge layer.

2. The article of claim 1, wherein the plurality of barriers includes barriers in the form of parallel lines.

3. The article of claim 1, wherein the plurality of barriers includes barriers in the form of a plurality of lines disposed at a non-orthogonal angle to the longitudinal direction.

4. The article of claim 1, wherein the article is a diaper, a training pant, an adult incontinent garment, or a menstrual pad.

5. The article of claim 1, wherein the plurality of barriers includes a plurality of embossments.

6. The article of claim 1, wherein the plurality of barriers include one of an embossment, a blocking filler, a chemical treatment, a slit, a film fragment, a polymeric material, an adhesive, a lotion, an ointments, and combinations thereof.

7. An absorbent article comprising:
   a bodyside liner;
   an outer cover;
   an absorbent body disposed between the bodyside liner and the outer cover; and
   a surge layer disposed between the bodyside liner and the absorbent body, the surge layer having an X-Y plane, a Z-direction, and a longitudinal direction, and a plurality of barriers extending substantially through the surge layer in the Z-direction, wherein the plurality of barriers is configured to block all linear longitudinal fluid flow paths within the surge layer itself while allowing non-linear fluid flow paths in the longitudinal direction.

8. The article of claim 7, wherein the article is a diaper, a training pant, an adult incontinent garment, or a menstrual pad.

* * * * *